United States Patent
Grabowski et al.

(10) Patent No.: US 7,435,853 B2
(45) Date of Patent: Oct. 14, 2008

(54) PROCESS FOR THE PRODUCTION OF DI- AND POLYAMINES OF THE DIPHENYLMETHANE SERIES

(75) Inventors: Stefan Grabowski, Dormagen (DE); Markus Dugal, Kempmen (DE); Aurel Wolf, Wülfrath (DE)

(73) Assignee: Bayer MaterialScience AG, Leverkusen (DE)

( * ) Notice: Subject to any disclaimer, the term of this patent is extended or adjusted under 35 U.S.C. 154(b) by 6 days.

(21) Appl. No.: 11/350,641

(22) Filed: Feb. 9, 2006

(65) Prior Publication Data

US 2006/0183938 A1 Aug. 17, 2006

(30) Foreign Application Priority Data

Feb. 15, 2005 (DE) ............ 10 2005 006 692

(51) Int. Cl.
*C07C 211/13* (2006.01)
*C07C 211/26* (2006.01)
*C07C 211/27* (2006.01)

(52) U.S. Cl. ............ 564/331; 564/330; 564/332; 564/333

(58) Field of Classification Search ............ 560/25
See application file for complete search history.

(56) References Cited

U.S. PATENT DOCUMENTS

| | | | |
|---|---|---|---|
| 2,519,788 A | 8/1950 | Payne | 260/603 |
| 3,272,865 A | 9/1966 | Barker | 260/581 |
| 4,010,208 A | 3/1977 | Aicher et al. | 260/603 HF |
| 4,265,834 A | 5/1981 | Birkenstock et al. | 564/421 |
| 4,705,883 A * | 11/1987 | Grate et al. | 560/25 |
| 6,031,136 A * | 2/2000 | Renbaum et al. | 564/333 |
| 6,639,102 B2 | 10/2003 | Hagen et al. | 560/347 |
| 2003/0176626 A1 | 9/2003 | Hagen et al. | 528/310 |
| 2005/0113557 A1 | 5/2005 | Dugal | 528/310 |

FOREIGN PATENT DOCUMENTS

GB 1080508 8/1967

OTHER PUBLICATIONS

Prati et al Catalytic hydrogen-transfer reduction . . . Gazzeta chimica Italiana 122, 1992, p. 221223.*
The Merck index, p. 1262, Merck &Co, 1996.*
Saunders Organic polymer chemistry, Chapman and Hall, Ltd, 1973, p. 315-316.*
Hydrocarbon Processing, 59, No. 11, Nov. 1979, p. 136, "Aniline".
Winnacker-Küchler Chemische Technologie, 3$^{rd}$ ed., vol. 4, (date unavailable) p. 170-171, "Anilin".
Gazzetta Chimica Italiana, 122, (month unavailable) 1992, pp. 221-223, Laura Prati et al, "Catalytic Hydrogen-Transfer Reduction of Organic Molecules with Methanol as Hydrogen Source".

* cited by examiner

*Primary Examiner*—Rabon Sergent
*Assistant Examiner*—Gregory Listvoyb
(74) *Attorney, Agent, or Firm*—Lyndanne M. Whalen; N. Denise Brown

(57) ABSTRACT

Di- and polyamines of the diphenylmethane series are produced by
a) converting nitrobenzene and methanol in the presence of a catalyst to aniline, formaldehyde and carbon monoxide, and then
b) converting the aniline and formaldehyde produced in step a) in the presence of an acid catalyst to di- and polyamines of the diphenylmethane series, and
c) converting the carbon monoxide produced in step a) with chlorine to phosgene.

7 Claims, No Drawings

PROCESS FOR THE PRODUCTION OF DI- AND POLYAMINES OF THE DIPHENYLMETHANE SERIES

BACKGROUND OF THE INVENTION

The present invention relates to a process for the production of di- and polyamines of the diphenylmethane series (MDA) by reaction of aniline with formaldehyde, in which the mixture of aniline and formaldehyde required for production is produced in the volume ratio required for MDA production simultaneously from the starting compounds nitrobenzene and methanol.

Aniline and formaldehyde are important intermediate products for the polymer industry among other things. Aniline and formaldehyde are used together, for example, as starting materials for the production of methylene diphenyl diamine (MDA) and the corresponding polyamines, and methylene diphenyl diisocyanate (MDI) and the corresponding polyisocyanates, an important monomer for the production of polyurethane. There are a number of processes for the production of aniline and formalin respectively, some of which have been used industrially. Aniline is currently produced industrially by the catalytic gas phase hydrogenation of nitrobenzene with hydrogen in adiabatic (Hydrocarbon Process 59 (Nov. 1979) no. 11, 136; U.S. Pat. No. 3,636,152) or isothermal operation (U.S. Pat. No. 4,265,834) using a Cu or Pd catalyst. The reduction of nitrobenzene with iron (Bechamp process, *Winnacker-Küchler Chemische Technologie*, $3^{rd}$ ed., Vol. 4, pp. 170-171) and the heterogeneously-catalyzed gas phase ammonolysis of phenol (Halcon process, U.S. Pat. No. 3,272,865) are of secondary importance.

The production of formaldehyde on an industrial scale is currently carried out substantially by silver-catalyzed dehydrogenation processes (DE-A-2 322 757, U.S. Pat. No. 2,519,788) and the so-called Formox process (GB-A-1 080 508).

In the silver-catalyzed process, methanol is dehydrogenated by air at >600° C. on a silver catalyst with the formation of formaldehyde and hydrogen, the hydrogen being converted to water with atmospheric oxygen in the further course of the reaction or in subsequent reaction stages for the purposes of energy production. The Formox process comprises a two-stage oxidation of methanol to formaldehyde and water (oxidation-reduction cycle of the catalyst), which takes place at lower temperatures in the range 270-300° C., as a rule using molybdenum-iron catalysts.

When the above-described processes are used, the aniline and formaldehyde must be produced and processed independently of each other in separate units. For the production of aniline, particularly by the industrially-definitive hydrogenation process, hydrogen must also be used as a cost-intensive reducing agent.

For the production of methylene diphenyl diisocyanate and the corresponding polyisocyanates (MDI), MDA is reacted with phosgene. The phosgene required for phosgenation is conventionally produced by an industrial process in which carbon monoxide and chlorine are fed over activated charcoal and reacted in the process. The reaction is highly exothermic. Conventionally, a cooled tube bundle reactor is used, the tubes of which are packed with granulated activated charcoal. The temperature of the activated charcoal bed in the reaction zone is about 400° C. and drops by cooling along the tubes to 40-150° C. It is also possible to carry out the reaction in two stages, the first being carried out at a high temperature (200-400° C.) and the second at a lower temperature (40-150° C.). In the majority of applications, the lowest possible residual chlorine content is desirable. Carbon monoxide is thus conventionally used in stoichiometric excess. The reaction is carried out at atmospheric pressure. The gaseous phosgene formed is absorbed in solvent in a further process step. This solution is then used in the production of the isocyanates by reaction with di- and/or polyamines.

For the production of MDA by acid-catalyzed reaction of aniline and formaldehyde, it would be advantageous to produce aniline and formaldehyde simultaneously in a single process, so that fewer unit parts are required and the process is simplified. Furthermore, it would be advantageous from an economic and process safety point of view to replace the hydrogenation hydrogen in the nitrobenzene reduction to aniline with a source of hydrogen that is cheaper and easier to handle, and which also transfers/hydrogen under formation of a useful material.

It has been found that the objects described above can be achieved by the catalytic transfer hydrogenation of nitrobenzene and methanol according to equation (I)

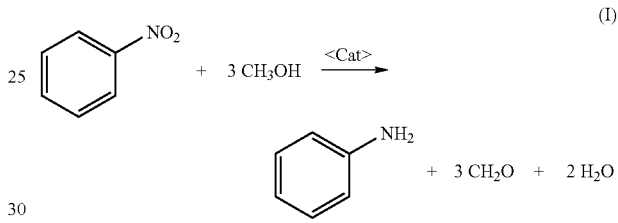

However, a mixture produced according to equation (I) has a molar ratio of aniline to formaldehyde of 1:3, while mixtures with a molar ratio of aniline to formaldehyde of 1.5:1 to 10:1 (correspondingly 1:0.1 to 1:0.67) are conventionally used for industrial synthesis of MDA. Aniline is conventionally not fully converted in this process, so that part of the aniline used can be re-circulated after the reaction. This re-circulated part of the aniline is conventionally supplemented with fresh aniline and converted again with formaldehyde to MDA. A molar ratio of 0.9:1 to 2.4:1 (correspondingly 1:1.1 to 1:0.42) is set industrially for the fresh portions of the aniline and the formaldehyde used in the reaction.

Product mixtures that are obtained according to equation (I) should therefore be supplemented with a significant additional quantity of aniline that has been produced by a conventional process, so that these mixtures are suitable for industrial MDA synthesis. However, this significantly reduces the economy of the process, as conventional nitrobenzene hydrogenation also remains necessary in addition to transfer hydrogenation according to equation (I).

SUMMARY OF THE INVENTION

The object of the present invention was thus to provide a simple and economic process for the production of MDA, in which the use of aniline that has been produced by hydrogenation of nitrobenzene can be eliminated.

This and other objects which will be apparent to those skilled in the art are accomplished by (1) converting nitrobenzene and methanol to aniline, formaldehyde and carbon monoxide, (2) converting the aniline and formaldehyde from (1) to an amine and (3) reacting the carbon monoxide from (1) with chlorine to form phosgene.

DETAILED DESCRIPTION OF THE INVENTION

The invention relates to a process for the production of di- and polyamines of the diphenylmethane series, in which a) nitrobenzene and methanol are converted in the presence of a catalyst to aniline, formaldehyde and carbon monoxide and then b) the aniline and formaldehyde produced in step a) are converted in the presence of an acid catalyst to di- and polyamines of the diphenylmethane series, and c) the carbon monoxide produced in step a) is converted to phosgene with chlorine.

In step a) the following reactions in particular may take place, in addition to other reactions:

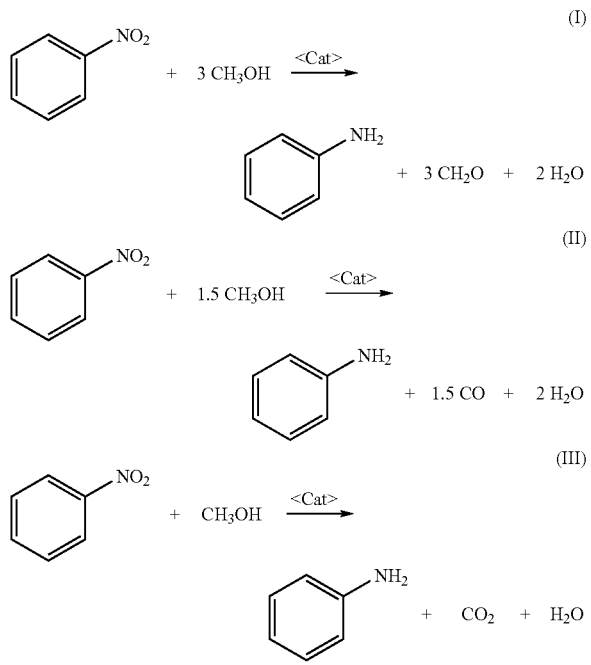

The reactions shown in equations (I) to (III) may take place directly in the manner shown. However, it is also possible for the formation of CO according to equation (II), for example, to take place via formaldehyde as an intermediate stage or for the formation of $CO_2$ to take place via formaldehyde and/or CO as an intermediate stage. Equally, it is possible that other intermediate and secondary products may form besides CO, in which the carbon is present in the oxidation stage –2, e.g. formic acid and its organic and/or inorganic derivatives. Furthermore, it is possible that other intermediate and secondary products may form besides $CO_2$, in which the carbon is present in the oxidation stage –4, e.g. carbonic acid and its organic and/or inorganic derivatives such as carbonates, carbamates, ureas, and isocyanates.

The production of aniline by catalytic transfer reduction of nitrobenzene with methanol is described by Rossi et al. (Gaz. Chim. It., 122, 1992, 221-223). Here, a Cu catalyst is used at temperatures of 180° C. Aniline is the sole reaction product with a conversion of 58%. However, Rossi et al. discuss the theoretical possibility that formaldehyde, methyl formate, CO and $CO_2$ could form as by-products of the reaction although no experimental proof of this is given. The possibility of obtaining, by the transfer reduction of nitrobenzene with methanol, a reaction product mixture containing aniline and formaldehyde with a composition that would allow direct use for the production of MDA is not considered in Gaz. Chim. It., 122 1992, 221-223.

Suitable catalysts for the transfer reduction of nitrobenzene in step a) are, for example, inorganic catalysts insoluble in the reaction medium (heterogeneous) or soluble (homogeneous) metal complexes or salts, these catalysts containing one or more metals as catalytically active components in elementary or bonded form. Suitable metals are for example Pd, Pt, Rh, Ir, Ru, Fe, Co, Ni, Cu, Al, Mg, Zr, Zn, V, Cr, Mo, W, Pb, and lanthanoids. Pd, Pt, Ir, Ru, Cu, Ni, or Fe-containing catalysts are preferably used.

The reaction of nitrobenzene with methanol in step a) preferably takes place in the presence of auxiliary substances. Suitable auxiliary substances are, for example, basic inorganic or organic compounds that are- soluble or insoluble in the reaction medium or solvents. Suitable bases include: hydroxides such as NaOH, KOH or $NI_4OH$; carbonates such as $Na_2CO_3$ or $K_2CO_3$; hydrogen carbonates such as $NaHCO_3$; amines such as triethylamine or aniline; or insoluble basic solids such as hydrotalcite, $Al_2O_3$, and MgO. Insoluble basic solids may optionally be used simultaneously as bases and as support materials for the catalyst. Preferred bases are NaOH, KOH, hydrotalcite or aluminum oxide.

Suitable solvents include water, alcohols, organic amines and/or nitro compounds. Preferred solvents are the components methanol, nitrobenzene, water and aniline participating in the reaction.

The reaction can generally be carried out in the gas and/or liquid phase. Suitable reaction temperatures are conventionally in the range of 20° C.-500° C., preferably in the range of 50° C.-300° C. The absolute reaction pressure is conventionally in the range of 0.1 bar to 300 bar, preferably in the range of 1 bar to 100 bar. The concentrations and concentration ratios of the starting compounds and the auxiliary substances can, in principle, be selected freely. Depending on the choice of reaction conditions, partial or full conversion in relation to methanol or nitrobenzene can be achieved in the reaction.

The product mixture produced by the process according to the invention preferably has a molar ratio of aniline to formaldehyde of 0.9:1 to 2.4:1 and a molar ratio of aniline to CO of 10:1 to 0.5:1.

Methanol and nitrobenzene are preferably used in a molar ratio of 3:1 to 10:1 in the reaction. The product mixture obtained from the reaction after cooling to ambient temperature (25° C.) and de-pressurizing to atmospheric pressure, is composed of a gas phase, containing carbon monoxide, carbon dioxide and optionally other gaseous components (e.g., hydrogen) and a liquid phase, containing aniline and formaldehyde, optionally excess methanol and optionally excess nitrobenzene, and also optionally formed by-products such as N-methyl aniline, toluidine, N-formyl aniline, N-phenylmethyl carbamate, aminobenzyl aniline, etc.

The aniline and formaldehyde reaction products, the secondary components optionally arising, any un-converted nitrobenzene and methanol, and also the auxiliary substances used may be partially or fully separated off from the reaction mixture and optionally processed to the pure compound(s). Aniline and/or formaldehyde obtained in this way can be used in principle for other applications besides MDA production. Optionally isolated secondary compounds such as $CO_2$ are, in principle, also available for other applications. Unconverted nitrobenzene and/or methanol are preferably re-circulated into the reaction cycle. CO is also removed from the reaction mixture, for example by gas separation, and optionally purified for example by low-temperature condensation and fractionation, an adsorption/desorption process or similar process, before conversion with chlorine into phosgene in step c).

Alternatively, the aniline and formaldehyde reaction products together with the unconverted starting compounds nitrobenzene and methanol and also optionally the auxiliary substances can be fully or partially left in the reaction mixture and converted directly to MDA in step b).

In step b), the aniline and formaldehyde produced in step a) are further converted to MDA, optionally after prior purification. For this purpose, an acid catalyst is added to the mixture containing aniline and formaldehyde.

Suitable acid catalysts are strong, organic or inorganic acids. Examples of suitable acids include: hydrochloric acid, sulfuric acid, phosphoric acid, methanesulfonic acid and solid acids such as zeolites. Hydrochloric acid is preferably used.

After mixing, the reaction mixture is generally subjected to a preliminary reaction in the temperature range of from 20° C. to 100° C., preferably from 30° C. to 80° C. and then, in stages or continuously, and optionally under excess pressure, brought to a temperature of 100° C. to 250° C., preferably to 100° C. to 180° C., most preferably to a temperature of 100° C. to 160° C. The preliminary reaction can, however, also be eliminated.

The reaction mixture obtained is then preferably neutralized with a base and separated into the aqueous and the organic phases in a separation vessel. The MDA is then contained in the organic phase.

In addition to the mixture of aniline and formaldehyde, which is obtained in a suitable molar ratio for MDA production, CO is also formed in step a) according to the invention. The CO thus produced is then converted with chlorine to phosgene in step c). A suitable process for the production of phosgene from CO and chlorine is disclosed for example in EP-A-134 506. In this process, CO and chlorine are reacted in tube bundle reactors on activated charcoal catalysts at temperatures of less than 100° C. at the reactor outlet. In a preferred embodiment, the phosgene thus produced is used for the phosgenation of the MDA produced in step b) to MDI.

The invention further relates to a process for the production of di- and polyisocyanates of the diphenylmethane series, in which
a) nitrobenzene and methanol are converted in the presence of a catalyst to aniline, formaldehyde and carbon monoxide and then,
b) the aniline and formaldehyde produced in step a) are converted in the presence of an acid catalyst to di- and polyamines of the diphenylmethane series, and
c) the carbon monoxide produced in step a) is converted with chlorine to phosgene, and
d) the di- and polyamines of the diphenylmethane series produced in step b) are converted by phosgenation to the di- and polyisocyanates of the diphenylmethane series.

For this purpose, in addition to the process for the production of di- and polyamines of the diphenylmethane series described above (steps a) to c)), the MDA produced in step b) is then converted with phosgene in an inert organic solvent by the known methods to the corresponding isocyanates. The molar ratio of raw MDA from step b) to phosgene is usefully measured in such a way that for each mol of $NH_2$ groups from 1 to 10 mol, preferably from 1.3 to 4 mol of phosgene are present in the reaction mixture. Chlorinated, aromatic hydrocarbons such as monochlorobenzene, dichlorobenzenes, trichlorobenzenes, the corresponding toluenes and xylenes and also chloroethylbenzene have proven to be useful as inert solvents. In particular, monochlorobenzene, dichlorobenzene or mixtures of these chlorobenzenes, are used as inert organic solvents. The quantity of solvent is generally measured in such a way that the reaction mixture has an isocyanate content of 2 to 40 wt. %, preferably 5 to 20 wt. % in relation to the total weight of the reaction mixture. Once phosgenation is complete, the excess phosgene, the inert organic solvent or mixtures thereof are separated from the reaction mixture by distillation.

Having thus described the invention, the following Examples are given as being illustrative thereof.

EXAMPLES

Example 1a

According to the Invention

Catalyst: 5 wt. % Pd on aluminum oxide 1.233 g nitrobenzene, 3.232 g methanol and 0.119 g palladium catalyst (5 wt. % Pd on basic aluminum oxide) were provided in a mixing vessel of VA steel. The vessel was sealed and brought to reaction in an oil bath with magnetic stirring at 195° C. for 150 min under pressure. The sealed vessel was then cooled to room temperature, a sample was taken from the gas chamber and it was then de-pressurized to atmospheric pressure. The catalyst was centrifuged off and the remaining solution was separated out.

The analysis of the gas sample and the liquid reaction mixture showed that the following products formed:

| | |
|---|---|
| Aniline | 0.80 mmol |
| Formaldehyde | 0.532 mmol |
| CO | 0.53 mmol |
| $CO_2$ | 0.19 mmol |

The molar ratio of aniline:formaldehyde was thus 1.50, the molar ratio of aniline to CO was 1.51.

Examples 1b to 11 were carried out in corresponding manner and the results of these are summarized in Table 1. When using mixed metal catalysts, the ratios of the proportions by weight of the metal components are also given.

TABLE 1

| | Cat | | Weighed portions [g] | | | Reaction Conditions | | Composition of Product Mixture [mmol] | | | | | | |
|---|---|---|---|---|---|---|---|---|---|---|---|---|---|---|
| | Metal (5 wt. %) | Support | Cat | Nitro-benzene | Methanol | Time [min] | Temp. [° C.] | Aniline | Nitro-benzene | Formal-dehyde | CO | $CO_2$ | Aniline:formal-dehyde | Aniline:CO |
| a | Pd | Aluminum oxide | 0.119 | 1.23 | 3.23 | 150 | 195 | 0.80 | 8.69 | 0.53 | 0.53 | 0.19 | 1.51 | 1.51 |

TABLE 1-continued

| | Cat | | Weighed portions [g] | | | Reaction Conditions | | Composition of Product Mixture [mmol] | | | | | | |
|---|---|---|---|---|---|---|---|---|---|---|---|---|---|---|
| | Metal (5 wt. %) | Support | Cat | Nitro-benzene | Methanol | Time [min] | Temp. [° C.] | Aniline | Nitro-benzene | Formal-dehyde | CO | CO$_2$ | Aniline:formal-dehyde | Aniline:CO |
| b | Pd/Ni 1:1 | Aluminum oxide | 0.160 | 1.23 | 3.22 | 140 | 190 | 0.88 | 9.12 | 0.58 | 0.36 | 0.10 | 1.52 | 2.44 |
| c | Pd | Aluminum oxide | 0.448 | 1.24 | 3.22 | 140 | 187 | 2.01 | 7.59 | 1.05 | 1.08 | 0.55 | 1.91 | 1.86 |
| d | Pd | Aluminum oxide | 0.142 | 1.24 | 2.69 | 162 | 190 | 1.04 | 9.03 | 0.68 | 0.54 | 0.12 | 1.53 | 1.93 |
| e | Pd/Ir 96:4 | Aluminum oxide | 0.298 | 1.24 | 2.71 | 159 | 190 | 1.36 | 8.06 | 0.71 | 0.89 | 0.50 | 1.92 | 1.53 |
| f | Pd/Ir 3:1 | Hydrotalcite | 0.253 | 1.24 | 3.22 | 130 | 190 | 3.16 | 6.33 | 1.32 | 0.38 | 1.26 | 2.39 | 8.32 |
| g | Pd/Ir 1:1 | Aluminum oxide | 0.579 | 1.24 | 3.26 | 140 | 185 | 1.06 | 8.70 | 0.60 | 0.39 | 0.60 | 1.77 | 2.72 |
| h | Pd/Ni 3:1 | Aluminum oxide | 0.372 | 1.23 | 1.61 | 170 | 170 | 1.06 | 8.89 | 0.59 | 0.28 | 0.27 | 1.80 | 3.79 |
| i | Pd/Ru 6:4 | Aluminum oxide | 0.330 | 1.23 | 1.62 | 130 | 180 | 0.96 | 8.96 | 0.45 | 0.23 | 0.16 | 2.13 | 4.17 |
| k | Pd/Ni 9:1 | Aluminum oxide | 0.415 | 1.23 | 1.62 | 120 | 180 | 1.25 | 8.29 | 0.62 | 0.17 | 0.12 | 2.02 | 7.35 |
| l | Pd/Ni 1:9 | Aluminum oxide | 0.259 | 1.23 | 3.22 | 180 | 200 | 1.16 | 8.56 | 0.56 | 0.58 | 0.22 | 2.07 | 2.00 |
| m | Pd/Cr/N 1:2:2.5 | Aluminum oxide | 0.261 | 1.23 | 6.41 | 60 | 195 | 0.996 | 8.85 | 0.54 | 1.21 | 0.044 | 1.86 | 0.82 |

A reaction mixture (804.2 g) of the following composition produced by catalytic transfer hydrogenation by the process according to the invention

| Aniline (wt. %) | Nitrobenzene (wt. %) | Formaldehyde (wt. %) | Methanol (wt. %) | Water (wt. %) |
|---|---|---|---|---|
| 12.4 | 45.9 | 1.8 | 35.8 | 4.1 | was further processed as follows:

Methanol and water were separated from this mixture by distillation. The remaining distillation bottom product (479.0 g) was tempered in a glass stirring apparatus with superimposition of nitrogen at 35° C. At this temperature, 11.4 g of 32.7% hydrochloric acid were added dropwise within 5 min. During this process the temperature was kept at 35° C. by an ice bath and stirring was continued at this temperature for 30 min. The mixture was then heated to 60° C. and stirring continued at this temperature for a further 30 min. The reaction charge was then heated to boiling and refluxed at boiling temperature (103° C.) for 10 h. 14.9 g 32% sodium hydroxide solution and 100 g of distilled water were then added and the two-phase mixture formed was thoroughly intermixed for 15 minutes. The phases were then separated and the organic phase was extracted twice more with 100 g distilled water each time. Excess aniline and also water and nitrobenzene were distilled off from the organic phase in a vacuum (0.1 mbar). The bottom temperature at the end of distillation was 215° C. The MDA produced (=distillation bottom product, 75.0 g) had the following composition:

| | Wt. % |
|---|---|
| Aniline | — |
| Nitrobenzene | — |
| 4,4'-MDA | 38.6 |
| 2,4'-MDA | 4.46 |
| 2,2'-MDA | 0.3 |
| N-methyl-MDA | 0.65 |
| 3-core-MDA | 19.9 |
| 4-core-MDA | 11.2 |
| Higher MDA oligomers | 15.3 |
| Other secondary components and unknown | 9.59 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of di- and polyamines of the diphenylmethane series comprising:
   a) converting nitrobenzene and methanol in the presence of a catalyst to aniline, formaldehyde and carbon monoxide, and then
   b) converting the aniline and formaldehyde produced in step a) in the presence of an acid catalyst to di- and polyamines of the diphenylmethane series, and
   c) converting the carbon monoxide produced in step a) with chlorine to phosgene in which the aniline and/or formaldehyde is partially removed from the aniline and formaldehyde produced in step a).

2. The process of claim 1 in which the catalyst used in step a) comprises a catalytically active composition containing at least one metal selected from Pd, Pt, Rh, Ir, Ru, Fe, Go, Ni, Cu, Al, Mg, Zr, Zn, V, Cr, Mo, W, Pb, and lanthanoids in elemental or bonded form.

3. The process of claim 1 in which step a) is carried out in the presence of a base.

4. A process for the production of di- and polyamines of the diphenylmethane series comprising:

a) converting nitrobenzene and methanol in the presence of a catalyst to aniline, formaldehyde and carbon monoxide, and then b) converting the aniline and formaldehyde produced in step a) in the presence of an acid catalyst to di- and polyamines of the diphenylmethane series, and c) converting the carbon monoxide produced in step a) with chlorine to phosgene in which the by-products formic acid and/or $CO_2$ and/or carbonates and/or formic acid methylester and/or N-formylaniline and/or N-methylaniline are partially or fully separated off from the aniline and formaldehyde produced in step a).

5. A process for the production of di- and polyamines of the diphenylmethane series comprising:

a) converting nitrobenzene and methanol in the presence of a catalyst to aniline, formaldehyde and carbon monoxide, and then b) converting the aniline and formaldehyde produced in step a) in the presence of an acid catalyst to di- and polyamines of the diphenylmethane series, and c) converting the carbon monoxide produced in step a) with chlorine to phosgene in which hydrochloric acid is used as the acid catalyst in step b).

6. A process for the production of di- and polyamines of the diphenylmethane series comprising:

a) converting nitrobenzene and methanol in the presence of a catalyst to aniline, formaldehyde and carbon monoxide, and then b) converting the aniline and formaldehyde produced in step a) in the presence of an acid catalyst to di- and polyamines of the diphenylmethane series, and c) converting the carbon monoxide produced in step a) with chlorine to phosgene in which aniline and formaldehyde are obtained in step a) in a molar ratio of from 0.9:1 to 2.4:1.

7. The process of claim 6 in which aniline and carbon monoxide are obtained in step a) in a molar ratio of from 0.5:1 to 10:1.

* * * * *